US005953428A

United States Patent [19]

Silverberg et al.

[11] Patent Number: 5,953,428

[45] Date of Patent: Sep. 14, 1999

[54] FEEDBACK METHOD OF NOISE CONTROL HAVING MULTIPLE INPUTS AND OUTPUTS

[75] Inventors: Michael H. Silverberg, Livingston, N.J.; Michael Anthony Zuniga, Fairfax, Va.

[73] Assignee: Lucent Technologies Inc., Murray Hill, N.J.

[21] Appl. No.: 08/640,199

[22] Filed: Apr. 30, 1996

[51] Int. Cl.[6] ...................... A61F 11/06

[52] U.S. Cl. ...................... 381/71.14; 381/71.8

[58] Field of Search ...................... 381/71, 94, 73.1, 381/93, 96, 94.1, 94.2, 94.3, 94.9, 71.1, 71.2, 71.8, 71.9, 71.14

[56] References Cited

U.S. PATENT DOCUMENTS

| | | | |
|---|---|---|---|
| 5,091,953 | 2/1992 | Tretter | 351/71 |
| 5,097,923 | 3/1992 | Ziegler et al. | 381/71 |
| 5,170,433 | 12/1992 | Elliott et al. | 381/94 |
| 5,394,376 | 2/1995 | Riddle et al. | 381/71.2 |

OTHER PUBLICATIONS

Elliott, S. J. et al., "A Multiple Error LMS Algorithm and Its Application to the Active Control of Sound and Vibration," *IEEE Transactions on Acoustics, Speech, and Signal Processing*, vol. ASSP-35, No. 10, Oct. 1987, pp. 1424–1434.

*Primary Examiner*—Vivian Chang

[57] ABSTRACT

A multidimensional feedback system is used to reduce the noise component of a vibrational or acoustic field. The feedback algorithm includes a matrix operator that diagonalizes the feedback system. As a consequence, each of two or more actuators can be treated as though it closes an independent, one-dimensional feedback system. Therefore, classical one-dimensional feedback analysis can be used in the context of a system having multiple error sensors and multiple actuators.

14 Claims, 5 Drawing Sheets

FEEDBACK METHOD OF NOISE CONTROL HAVING MULTIPLE INPUTS AND OUTPUTS

FIELD OF THE INVENTION

The present invention relates to the active control of acoustic or mechanical disturbances. More specifically, it relates to arrangements of multiple sensors and canceling actuators for controlling repetitive or non-repetitive phenomena that are described by a superposition of sinusoids of different frequencies, or in other words, that exhibit spectra displaying plural, narrowband tonals.

ART BACKGROUND

One approach to the problem of active noise control is described in "A Multiple Error LMS Algorithm and its Application to the Active Control of Sound and Vibrations," S. J. Elliott, I. M. Strothers, and P. A. Nelson, *IEEE Transactions on Acoustics, Speech and Signal Processing*, Vol. ASSP-35, No. 10, October 1987, pp. 1423–1434. A second approach is described in U.S. Pat. No. 5,091,953, issued to S. Tretter.

The article by Elliott et al. describes a time-domain approach in which a single reference signal derived from the noise source is passed through $N_a$ FIR filters whose taps are adjusted by an adaptive LMS algorithm. The approach assumes that the matrix of impulse responses relating the actuator and sensor signals are known. However, it is often difficult, in practice, to provide accurate estimates of these impulse responses. The Elliott et al. article does not offer any guidance for making these estimates.

U.S. Pat. No. 5,091,953 describes a cancellation arrangement using the well-known adaptive LMS algorithm to determine the optimal control signals to be sent to the actuators for each harmonic in the noise to be cancelled. However, this arrangement is limited in application to repetitive phenomena.

SUMMARY OF THE INVENTION

Such earlier approaches have attempted to determine optimal actuator-control signals through the use of adaptive algorithms. In accordance with the present invention, by contrast, these optimal signals are determined by processing the sensor signals in a manner that reduces the multi-dimensional active cancellation system to an equivalent collection of one-dimensional feedback systems. In this way, the well-known classical methods for determining the feedback gain (and hence, actuator signals) of a system with one sensor and one actuator are made applicable to an active cancellation system with a plurality of sensors and actuators.

This is achieved, in part, through the use of a feedback matrix. The feedback matrix relates each actuator-driving signal to a linear combination of error signals. The feedback matrix represents a diagonalization of the multi-dimensional active cancellation system in the sense that when the actuators are driven in accordance with this matrix, each actuator is at least approximately decoupled from the other actuators, and such actuator individually closes its own feedback loop.

Briefly, the present invention involves a method for reducing the noise component of a vibrational or acoustic field. This method involves sensing error signals at M discrete locations (M an integer greater than or equal to 2) and in response, constructing N corrective signals (N an integer greater than or equal to 2) for driving N respective electroacoustic or electromechanical actuators.

In accordance with the invention, each of the M error signals is subjected to a complex demodulation at each of L discrete disturbance frequencies (L an integer greater than or equal to 2) to produce L basebanded error signals per error-sensing location. For each disturbance frequency $\omega_l$ ($l$=1, . . . ,L), the corresponding M basebanded error signals are subjected to a feedback algorithm that results in a group of N basebanded corrective signals. Included in the feedback algorithm is a feedback matrix as described above. (A distinct such matrix is readily specified for each of the respective disturbance frequencies ($\omega_l$.)

The resulting basebanded corrective signals are remodulated to the original disturbance frequencies. A driving signal to each actuator is constructed by summing the L corresponding remodulated corrective signals (one said signal at each respective frequency $\omega_l$).

We have found that this approach permits very efficient digital processing relative to other methods of noise control.

DETAILED DESCRIPTION

Figure 1:
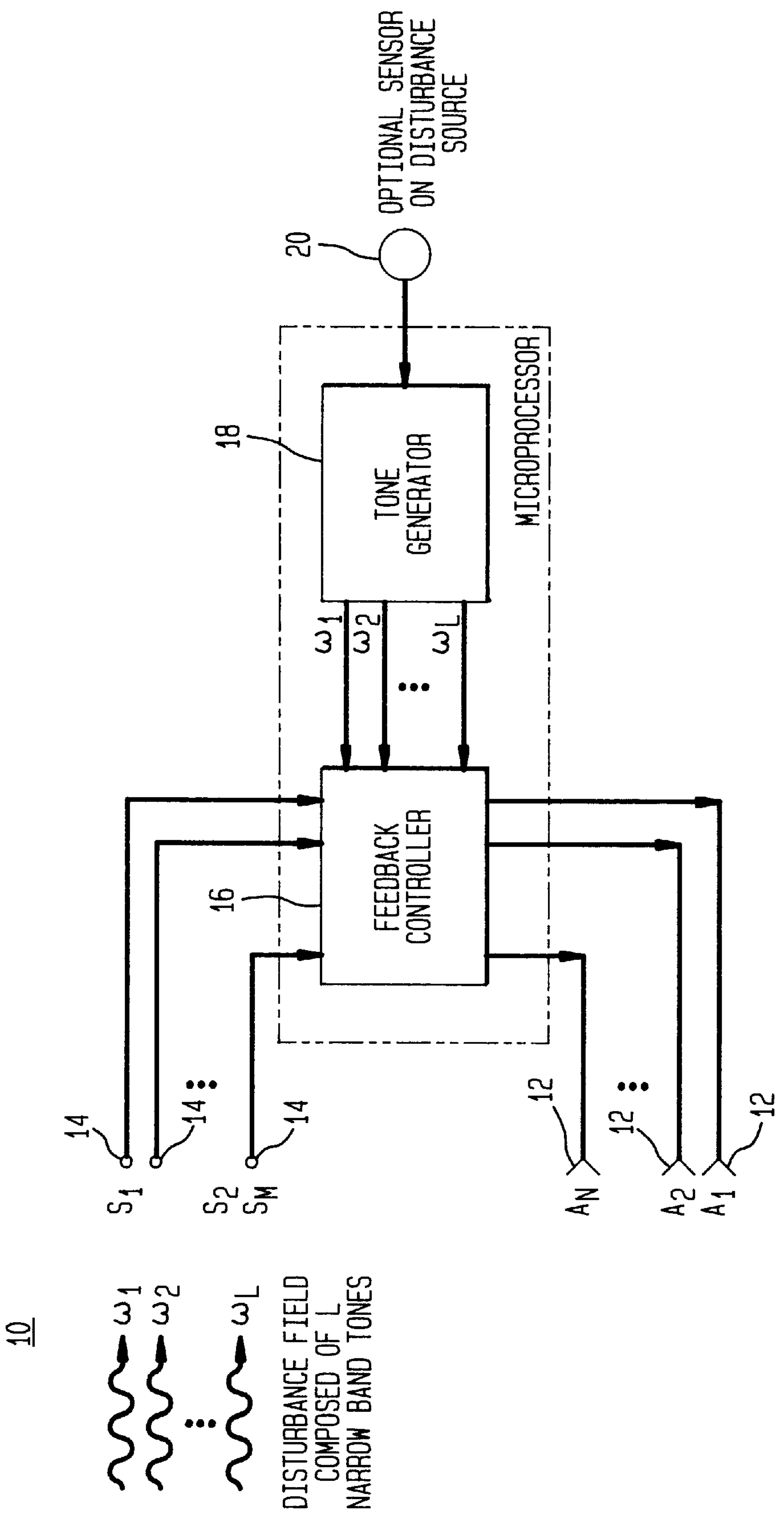
FIG. 1 is a schematic overview of a multidimensional feedback-control system according to the invention.

FIG. 1 depicts a disturbance field 10 composed of L narrowband (almost sinusoidal) tones and an arrangement for canceling the disturbance at several points in space using multiple actuators or loudspeakers 12, denoted ($A_1$, $A_2$, . . . , $A_N$), and multiple sensors 14, denoted ($S_1$, $S_2$, . . . , $S_M$).

A feedback controller 16, which is advantageously implemented on a microprocessor, processes the sensor signals and in response, generates actuator signals for controlling the actuators $A_1$, $A_2$, . . . , $A_N$.

A tone generator 18, which optionally receives input from a sensor at or near the disturbance source, produces L complex demodulation signals consisting of the cosine and sine pairs:

$$\cos(\omega_i t),\ \sin(\omega_i t),$$

where $\omega_i=2\pi f_i$, i=1, 2, . . . , L, and $f_i$ is the frequency of the $i^{th}$ narrowband disturbance.

An optional disturbance source sensor 20 is useful for detecting time-varying periodic disturbances such as those produced by an automobile engine and may, for example, consist of an engine tachometer whose output signal consists of P pulses per revolution. Thus, by counting the number of digital clock pulses that elapse between successive tachometer output pulses, it is possible to form an accurate estimate of the instantaneous fundamental rotational frequency $\Omega(t)$ of the engine, even during conditions of acceleration and deceleration. In at least some cases, this frequency $\Omega(t)$ will advantageously be treated as one of the disturbance frequencies, exemplarily the lowest of a harmonic series of disturbance frequencies, that are to be controlled.

The number of tachometer output pulses P per revolution should satisfy the criterion $$P > \frac{1}{2}\frac{\alpha}{\omega}\frac{\kappa}{f_h},$$

where $$\frac{\alpha}{\omega}$$

is the maximum expected acceleration-to-frequency ratio, $\kappa$ is the highest harmonic number expected, and $f_h$ is the bandwidth of filter h. This criterion ensures that the error in the estimated values of to $\omega_1$ (t) does not exceed the bandwidth of filter h. Typical values of P for automotive engine noise are 15–30.

If the tonal disturbances are harmonically related, the harmonic frequencies, $\omega_2, \omega_3, \ldots, \omega_L$, are readily determined by frequency multiplication. If, on the other hand, the tonal disturbances are stationary but not harmonically related, the frequencies $\omega_1, \ldots, \omega_L$ can be determined a priori by several well-known procedures for measurement and analysis, such as methods of spectral analysis.

Thus, the tone generator is readily implemented as an independent collection of L oscillators and 90° phase shifters, without necessarily including a disturbance source sensor.

As an aid to understanding the functioning of the inventive feedback controller, it is helpful to refer to the well-known one-dimensional, classical feedback controllers of the prior art. Such one-dimensional controllers, which have but one sensor and one actuator, are described, for example, in U.S. Pat. No. 2,983,790 issued to Olson, and in U.S. Pat. No. 4,489,441, issued to Chaplin.

The inventive feedback controller as depicted, for example, in FIG. 1 is also a classical feedback system, but it operates as a many-dimensional system rather than as a one-dimensional system. That is, feedback controller 16 operates to derive, from the error signals received from a plurality of sensors, plural actuator-control signals that will minimize the disturbance field simultaneously at the M sensor locations.

Figure 2:
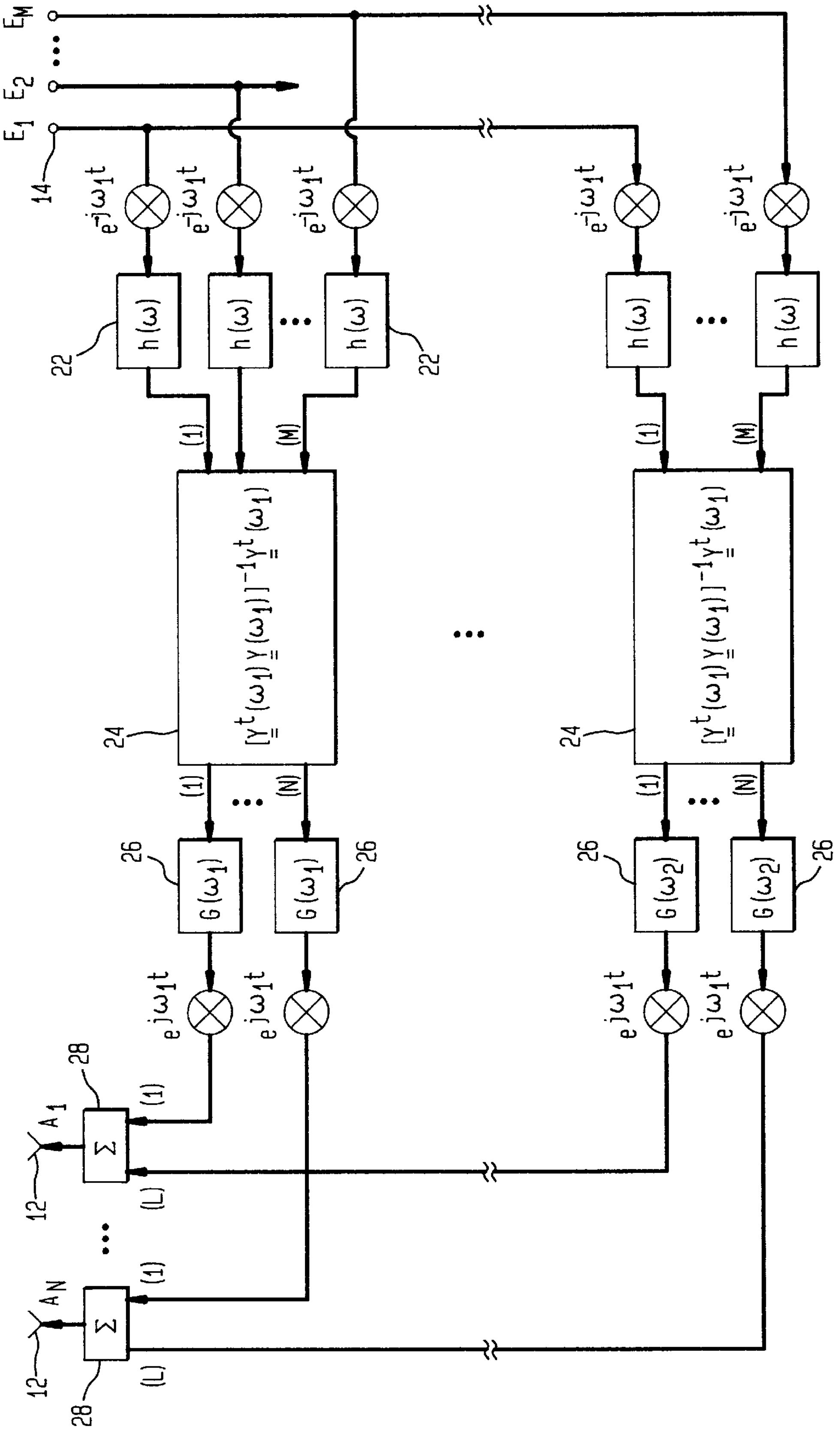
FIG. 2 is a schematic diagram illustrating the processing steps that take place in the operation of the control system of FIG. 1.

Referring to FIG. 2, error signals $E_1, E_2, \ldots, E_M$ are formed by superposition of the fields produced, respectively, by the disturbance and the actuators. These error signals are sensed by the respective sensors 14, and transmitted as M sensor signals to a digital signal processor, which makes up part of the feedback controller. The digital signal processor complex-demodulates the sensor signals to baseband at each of the L disturbance frequencies by multiplying each of the M signals by each of the L respective cosine-sine pairs produced by the tone generator. (This procedure is mathematically equivalent to multiplying each error signal by the complex signal $e^{-j\omega_l t}$ at the $l^{th}$ disturbance frequency.) This produces, for each of the L disturbance frequencies, a group of M basebanded tonal error signals.

The M basebanded tonal error signals (for each disturbance frequency) are then low pass filtered, as indicated by the blocks 22 labeled $h(\omega)$, to remove undesired frequency content. The low pass filter $h(\omega)$ is exemplarily a single pole filter having the transfer function:

$$h(\omega) = \frac{1}{1 + j\omega\tau},$$

where $\tau$=the filter time constant.

The magnitude of filter time constant $\tau$ is chosen to provide adequate rejection of neighboring tonals.

For each disturbance frequency $\omega_1, \omega_2, \ldots, \omega_L$, the corresponding M basebanded tonal error signals are related to a group of N basebanded tonal actuator signals through the matrix transformation $[\underline{\underline{Y}}^t(\omega_l)\underline{\underline{Y}}(\omega_l)]^{-1}\underline{\underline{Y}}^t(\omega_l)$, represented as box 24 in FIG. 2.

The purpose of this matrix transformation is: (i) to extract the controllable part of the error signals, and then (ii) to diagonalize and normalize the resulting multidimensional feedback system. The physical significance of this is that a unit basebanded drive signal to the $n^{th}$ actuator at the $l^{th}$ disturbance frequency will elicit from box 24 a unit basebanded output signal only in the $n^{th}$ channel.

The expression $\underline{\underline{Y}}(\omega_l)$, referred to as the "plant matrix," or "transfer function matrix," represents the M×N matrix of transfer functions between each of the N actuators and M sensors evaluated at disturbance frequency $\omega_l$(l=1, 2, . . . , L). This matrix acts upon the input to box 24 to extract the controllable part of the error signals. $\underline{\underline{Y}}^t(\omega_l)$ is the transpose-complex conjugate of $\underline{\underline{Y}}(\omega_l)$.

The expression $[\underline{\underline{Y}}^t(\omega_l)\underline{\underline{Y}}(\omega_l)]^{-1}\underline{\underline{Y}}^t(\omega_l)$, is referred to as the "plant pseudoinverse."

As shown in blocks 26 of FIG. 2, a common feedback gain $G_l$ is readily applied at each disturbance frequency to the N basebanded signals. In accordance with well-known teachings in the art of classical feedback control, these gains are adjusted to provide a desired degree of noise cancellation and desired stability of the resulting feedback loop.

The basebanded tonal actuator signals are then remodulated in frequency by multiplication by $e^{+j\omega_l t}$. The control signal for each actuator is then formed by summing the appropriate remodulated signals over the L disturbance frequencies as shown in boxes 28 of FIG. 2.

Mathematically, the operation of the present invention may be described as follows. The disturbance field observed at the M error sensor locations consists of L narrowband tonals and may be represented by an M-dimensional column vector $\underline{d}(t)$, given by $$\underline{d}(t) = \begin{bmatrix} d_1(t) \\ d_2(t) \\ \vdots \\ d_M(t) \end{bmatrix} = \sum_{l=1}^{L} \underline{\hat{d}}_l(t) e^{j\omega_l t}, \tag{1}$$

where $$\underline{\hat{d}}_l(t) = \begin{bmatrix} \hat{d}_{1l}(t) \\ \hat{d}_{2l}(t) \\ \vdots \\ \hat{d}_{Ml}(t) \end{bmatrix} \tag{2}$$

is the vector of narrowband complex modulation coefficients at disturbance frequency $\omega_l$. Here, by "narrowband" is meant that the bandwidth $\Delta\omega_1, \Delta\omega_2, \ldots, \Delta\omega_L$ of the complex modulation coefficients is small enough, relative to the corresponding disturbance frequencies $\omega_1, \omega_2, \ldots, \omega_L$, that there is no substantial spectral overlap between modulated signals at neighboring disturbance frequencies.

From FIG. 2, it is clear that the control signals delivered to the N actuators may be represented by an N-dimensional column vector $\underline{c}(t)$ defined as:

$$\underline{c}(t)=\sum_{l=1}^{L} e^{j\omega_l t} g_l(t) * \left[\underline{\underline{Y}}^t(\omega_l)\underline{\underline{Y}}(\omega_l)\right]^{-1}\underline{\underline{Y}}^t(\omega_l)\cdot\hat{\underline{\epsilon}}_l(t), \tag{3}$$

where the symbol * denotes the convolution operation, and $g_l(t)$ is the impulse response associated with the feedback gain $G_l(\omega)$. In this expression, $\hat{\underline{\epsilon}}_l(t)$ is the vector representing the M complex demodulated and low-pass filtered narrow-band error signals centered at disturbance frequency $\omega_l$:

$$\hat{\underline{\epsilon}}_l(t)=h(t)*\underline{\epsilon}(t)e^{-j\omega_l t}, \tag{4}$$

and h(t) is the impulse response of the low pass filter h(ω).

The canceling field vector $\underline{C}(t)$ expected at the error sensors is calculated by convolving the actuator-to-sensor impulse-response-matrix $\underline{\underline{y}}(t)$ (which is simply the Fourier transform of $\underline{\underline{Y}}(\omega)$) with the control signal vector $\underline{c}(t)$:

$$\underline{C}(t)=\underline{\underline{y}}(t)*\underline{c}(t)= \sum_{l=1}^{L} e^{j\omega_l t}\underline{\underline{Y}}(\omega_l)\left[\underline{\underline{Y}}^t(\omega_l)\underline{\underline{Y}}(\omega_l)\right]^{-1}\underline{\underline{Y}}^t(\omega_l)\cdot g_l(t)*\hat{\underline{\epsilon}}_l(t). \tag{5}$$

Thus, the error signal vector $\underline{\epsilon}(t)$ is the difference between the disturbance and canceling field vectors:

$$\underline{\epsilon}(t)=\underline{d}(t)-\underline{C}(t). \tag{6}$$

By substituting Equation 6 into Equation 4, defining $$\hat{\underline{d}}_l(t)=h(t)*\underline{d}(t)e^{-j\omega_l t}, \tag{7}$$

and noting that the low-pass filter h(t) is designed to reject tonals not at baseband, it is readily demonstrated that $$\hat{\underline{\epsilon}}_l(t)=\hat{\underline{d}}_l(t)-\underline{\underline{Y}}(\omega_l)\,[\underline{\underline{Y}}^t(\omega_l)\underline{\underline{Y}}(\omega_l)]^{-1}\underline{\underline{Y}}^t(\omega_l)\cdot h(t)*g_l(t)*\hat{\underline{\epsilon}}_l(t). \tag{8}$$

Upon matrix multiplying both sides of Equation 8 on the left by $\underline{\underline{Y}}^t(\omega_l)$, the controllable error signal $\underline{e}_l(t)$ at disturbance frequency $\omega_l$ is derived as:

$$e_l(t)=\underline{\underline{Y}}^t(\omega_l)\hat{\underline{\epsilon}}_l(t)=\underline{\underline{Y}}^t(\omega_l)\hat{\underline{d}}_l(t)-h(t)*g_l(t)*\underline{e}_l(t). \tag{9}$$

By Fourier transforming Equation 9 and solving for the transform of $\underline{e}_l(t)$, denoted by $\tilde{\underline{e}}_l(\omega)$, L decoupled, one dimensional feedback equations are obtained:

$$\tilde{\underline{e}}_l(\omega)=\frac{\underline{\underline{Y}}^t(\omega_l)\tilde{\hat{\underline{d}}}_l(\omega)}{[1+h(\omega)G_l(\omega)]}.$$

Consequently, the cancellation level and stability of the proposed multi-dimensional active cancellation system can be determined by classical one-dimensional feedback system analysis.

In practice the L feedback loops may not be fully decoupled. Even if h has only a single pole, system delays can lead to a loop phase shift greater than 90°. However, suitable values for the filter bandwidth $f_h$ and the gain G will limit overall loop gain in the frequency region where individual loops overlap, thus ensuring stability.

In practice, the transfer function matrix $\underline{\underline{Y}}(\omega)$ is determined by sequentially exciting each actuator with either a swept sine wave or with pseudorandom noise over the total frequency band spanned by the disturbance tonals and then measuring the response at each of the error sensors. For example, if the $l^{th}$ actuator is excited by a sine wave of amplitude $A_l$ and frequency $\omega^r$, and if the measured base-banded response at sensor p is $V_p(\omega_r)$, then the transfer function $Y_{pl}(\omega_r)$ is given by $$V_p(\omega_r)=Y_{pl}(\omega_r)A_l,\ p=1, 2, \ldots, M;\ l=1, 2, \ldots, N. \tag{11}$$

By stepping the excitation frequency $\omega_r$ over the frequency band and repeating for all actuator-sensor pairs, the required transfer function matrix $\underline{\underline{Y}}(\omega)$ is obtained and stored in memory within the microprocessor.

It should be noted that if the number of actuators N is greater than the number of error sensors M, the matrix $[\underline{\underline{Y}}^t(\omega_l)\underline{\underline{Y}}(\omega_l)]$ is singular and not directly invertible. In this case, the box in FIG. 2 labelled $[\underline{\underline{Y}}^t(\omega_l)\underline{\underline{Y}}(\omega_l)]^{-1}\underline{\underline{Y}}^t(\omega_l)$ is replaced by a box that performs the operation:

$$\underline{\underline{Y}}^t(\omega_l)\,[\underline{\underline{Y}}(\omega_l)\underline{\underline{Y}}^t(\omega_l)]^{-1},\ N>M, \tag{12}$$

where $[\underline{\underline{Y}}(\omega_l)\underline{\underline{Y}}^t(\omega_l)]$ is not singular and hence invertible.

EXAMPLE

Figure 3A:
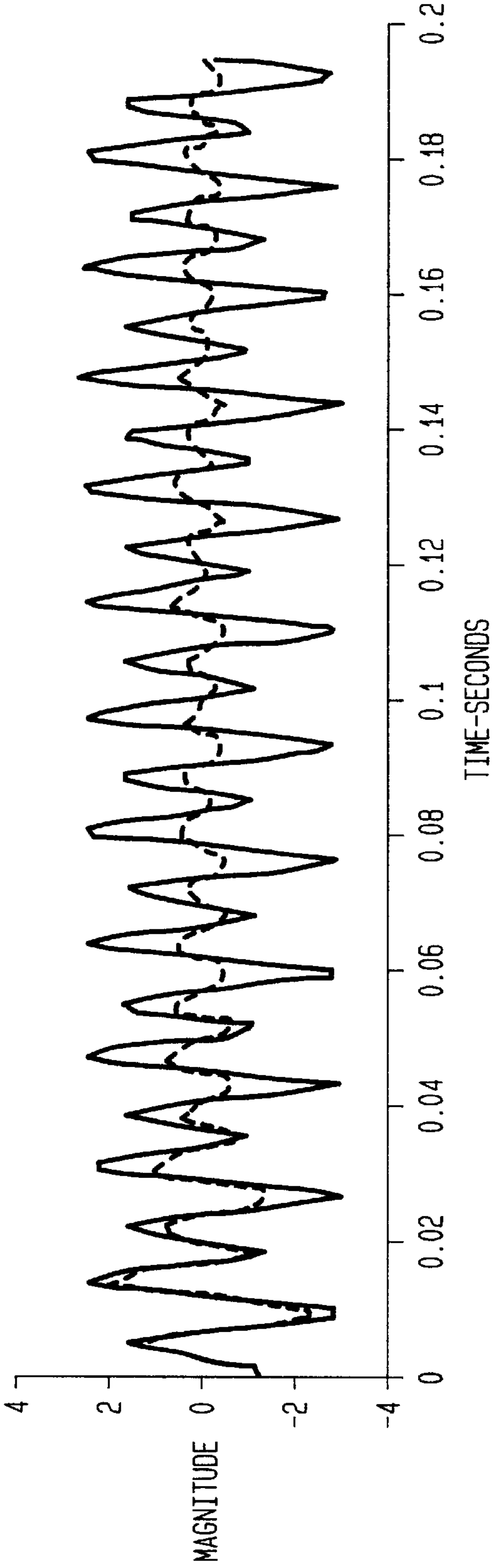
FIGS. 3A–3C illustrate the performance of an exemplary embodiment of the invention, as predicted by a computer simulation. Each of FIGS. 3A–3C is a graph of the predicted disturbance signal and residual signal at a respective one of three error sensors in a system having two actuators.
Figure 3B:
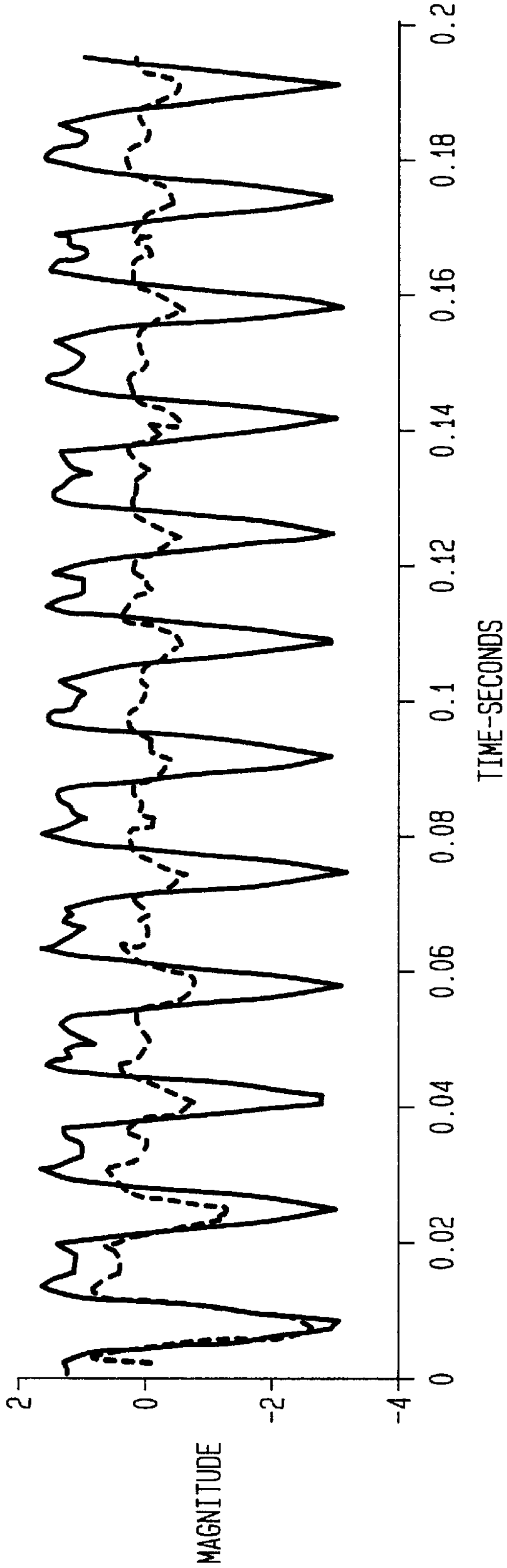
Figure 3C:
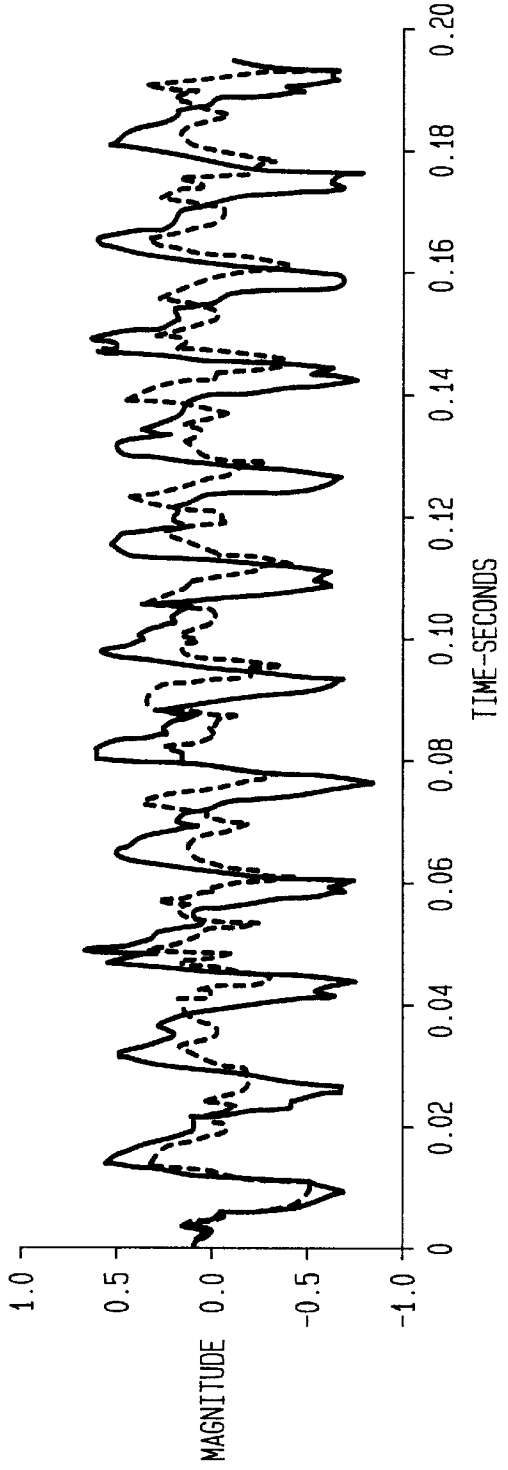

In order to verify overall performance of the inventive method, we performed several computational simulations. One such simulation included three sensors, two actuators and two frequencies. FIGS. 3A–3C show the disturbance and residual at each respective sensor as predicted by the simulation. It is evident from the figure that stability was achieved in about 0.1 second.

Figure 4A:
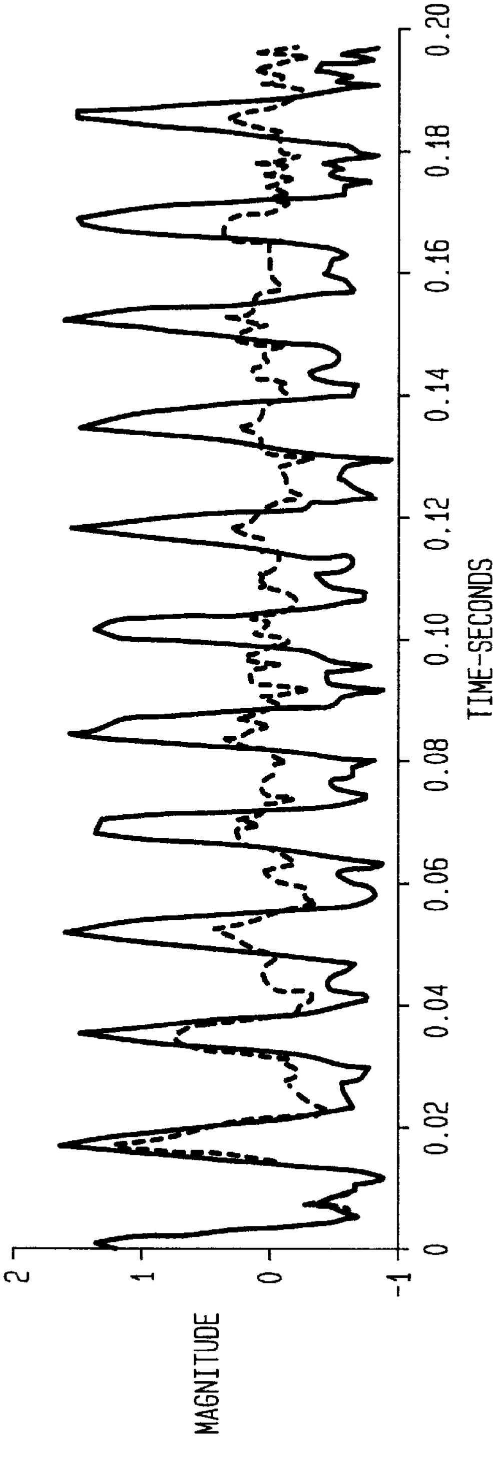
FIGS. 4A and 4B illustrate the performance of a second exemplary embodiment of the invention, as predicted by a computer simulation. Each of FIGS. 4A and 4B is a graph of the predicted disturbance signal and residual signal at a respective one of two error sensors in a system having three actuators.
Figure 4B:
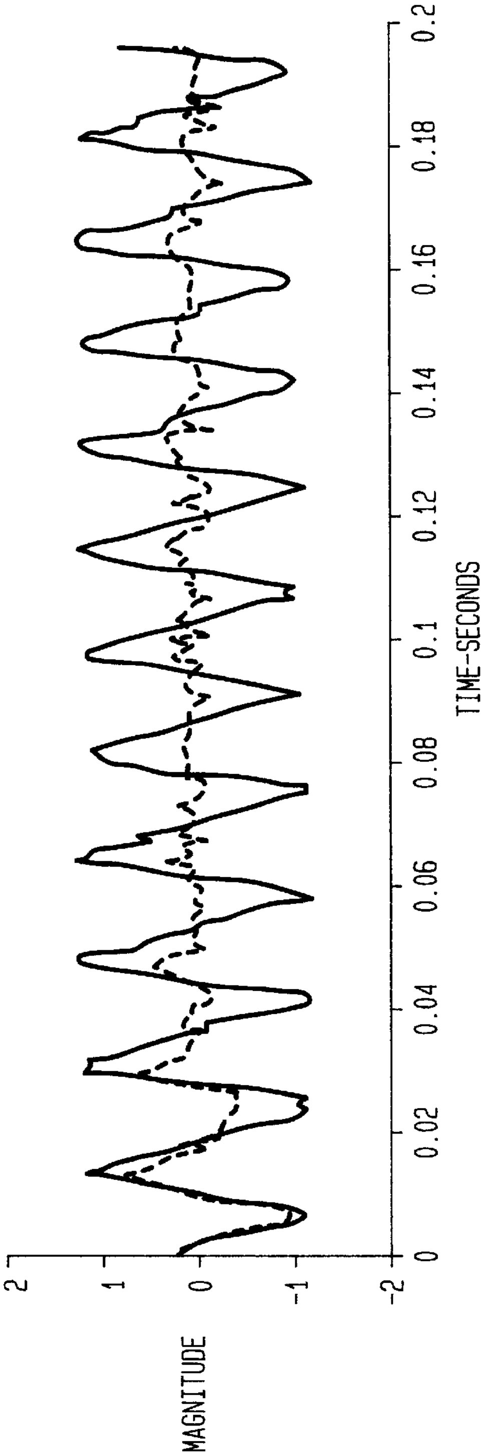
Figure 4C:
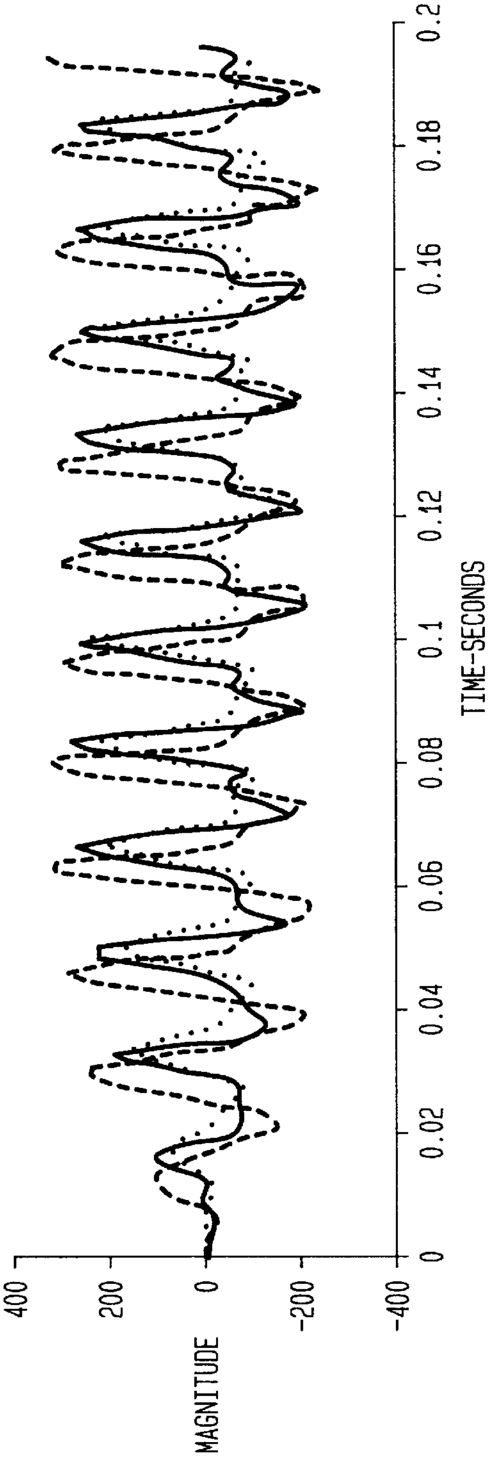
FIG. 4C is a graph of the three control signals that drive the three respective actuators in the control system of FIGS. 4A and 4B.

FIGS. 4A–4C show the results of a second simulation using two sensors and three actuators. FIGS. 4A and 4B show the disturbance and residual at each of the two respective sensors. FIG. 4C shows the three control signals that drove the three respective actuators. It is evident from a comparison of FIGS. 4A and 4B with FIGS. 3A–3C that a slightly higher degree of noise cancellation was predicted by the second simulation. This was to be expected, given that in the second instance, the number of actuators exceeded the number of sensors and afforded more degrees of freedom to the feedback controller.

The invention claimed is:

1. A method for reducing the noise component of a vibrational or acoustic field, comprising:

a) modeling the field at M sensor locations as an M dimensional column vector which is the sum of L narrowband complex modulation coefficients, each multiplied by a modulation signal having a frequency $\omega_l$, and selecting L discrete disturbance frequencies, $L\geqq 1$, such that there is no substantial spectral overlap between modulated signals at neighboring disturbance frequencies;

b) sampling the field at M discrete locations with M sensors, thereby to produce M respective error signals, $M\geqq 2$;

c) demodulating each said error signal with respect to each said frequency, thereby to produce a basebanded signal $\hat{d}_{ml}$, for each possible pair comprising an $m^{th}$ error signal and an $l^{th}$ frequency $\omega_1$, m=1, . . . ,M; l=1, . . . , L;

d) for each respective frequency $\omega_l$, forming N linear combinations of the M basebanded signals $\hat{d}_{ml}$, thereby to produce N basebanded actuator signals for each respective frequency $\omega_l$;

e) for each respective frequency $\omega_l$, remodulating the corresponding N basebanded actuator signals at said frequency $\omega_l$, thereby to produce N narrowband actuator signals $c_{n1}$ at each frequency $\omega_l$, n=1, . . . ,N:

f) for each respective value of n from 1 to N, summing the L narrowband actuator signals $c_{n1}$, thereby to construct N fullband actuator signals; and g) driving a respective one of N discretely situated electromechanical or electroacoustic actuators from each of the N fullband actuator signals, wherein h) the step of forming linear combinations of the basebanded error signals comprises combining said signals in accordance with matrix coefficients that include transfer functions for each actuator/sensor pair at each of the L frequencies and that are chosen to mutually decouple the N actuators such that each said actuator will behave at least approximately as part of a one-dimensional feedback loop.

2. The method of claim 1, further comprising:

applying to each basebanded actuator signal a gain coefficient adjusted to provide a desired degree of noise cancellation and a desired degree of stability of a resulting feedback loop.

3. The method of claim 2, wherein: M is greater than or equal to N;

for each respective frequency $\omega_l$, l=1, . . . ,L, values of a transfer function between each of M error sensors and each of N actuators at said frequency are represented by a transfer function matrix $\underline{\underline{Y}}(\omega_l)$;

said matrix has a transposed complex conjugate $\underline{\underline{Y}}^t(\omega_l)$; and the matrix coefficients chosen to mutually decouple the actuators are the coefficients of the matrix $[\underline{\underline{Y}}^t(\omega_l)\underline{\underline{Y}}(\omega_l)]^{-1}\underline{\underline{Y}}^t(\omega_l)$.

4. The method of claim 3, wherein said transfer-function values are determined by measuring the response of each error sensor to the output of each actuator when said actuator is driven by a signal at each frequency $\omega_l$.

5. The method of claim 2, wherein: N is greater than M;

for each respective frequency $\omega_l$, l=1, . . . ,L, values of a transfer function between each of M error sensors and each of N actuators at said frequency are represented by a transfer function matrix $\underline{\underline{Y}}((\omega_l)$;

said matrix has a transposed complex conjugate $\underline{\underline{Y}}^t(\omega_l)$; and the matrix coefficients chosen to mutually decouple the actuators are the coefficients of the matrix $\underline{\underline{Y}}^t(\omega_l)[\underline{\underline{Y}}(\omega_l)\underline{\underline{Y}}^t(\omega_l)]^{-1}$.

6. The method of claim 5, wherein said transfer-function values are determined by measuring the response of each error sensor to the output of each actuator when said actuator is driven by a signal at each frequency $\omega_l$.

7. The method of claim 1, wherein the number L of discrete frequencies is at least two, and the frequencies are harmonically related.

8. The method of claim 1, wherein the number L of discrete frequencies is at least two, and the frequencies are not harmonically related.

9. The method of claim 1, wherein the vibrational or acoustic field is generated by an automobile engine, and the method further comprises:

measuring a fundamental rotational frequency of the engine; and setting one of said discrete frequencies $\omega_l$ equal to said fundamental rotational frequency.

10. The method of claim 9, wherein said rotational frequency measurement comprises timing output pulses from an engine tachometer.

11. A noise cancellation system for actively reducing vibrations within a noise field, comprising:

N actuators situated within said noise field, said actuators connected to produce vibrational energy within said noise field, where N≧1;

M sensors operatively situated within said noise field to sample the field and to thereby produce M respective error signals, where M≧2; and where M does not have to be equal to N;

a controller coupled to said sensors to demodulate each of said error signals with respect to L demodulating signals, thereby producing a basebanded signal $d_{ml}$ for each possible pair of error signal and demodulating signals, with the L demodulating signals corresponding to disturbance frequencies and chosen such that there is no substantial spectral overlap between modulated signals at neighboring disturbance frequencies;

said controller further connected to perform a plant pseudoinverse operation on each of said basebanded signals, to apply a gain to the N resulting signal, to remodulate the N resultants at each disturbance frequency L, and to sum L respective resultants to form the drive signal for each of said N actuators.

12. A system for canceling the vibrational energy within a noise field, comprising:

N actuators connected to produce vibrations, N≧1;

M sensors connected to sense vibrations within the noise field and to thereby produce M error signals, M≧2; where M does not have to be equal to N; and a feedback controller connected to demodulate each of said M error signals with L demodulating frequencies, to extract the controllable part of said M error signals, to diagonalize and normalize the resulting multidimensional feedback system, to perform a plant pseudoinverse operation on each set of M demodulated error signals at each demodulating frequency, and to form L one dimensional feedback loops to control the vibration of said N actuators in response to said M error signals.

13. A system for cancelling signals within a disturbance signal field, comprising:

N actuators connected to produce cancellation signals, N≧1;

M sensors connected to sense signals within the disturbance signal field and to thereby produce M error signals, M≧2; where M does not have to be equal to N; and a feedback controller connected to demodulate each of said M error signals through multiplication by L demodulating complex signals of the form $e^{j\omega lt}$ and filtering the product of said multiplication by filters characterized by a transfer function h(ω), to diagonalize and normalize the demodulated signals and to thereby form L one dimensional feedback loops having transfer functions of the form $[\underline{Y}^t(\omega_l)d_l(\omega)][1+h(\omega)G_l(\omega)]$ where $\underline{Y}^t(\omega_l)$ is the transpose complex conjugate of the transfer function matrix composed of the transfer functions between each of the N actuators and M sensors evaluated at disturbance frequency $\omega_l$, $d_l(\omega)$ is the frequency response of the disturbance field vector, $h(\omega)$ is the frequency response of the demodulation filter, $G_l(\omega)$ is the frequency response of the loop feedback gain, and $[\underline{Y}^t(\omega_l)d_l(\omega)]$ denotes the dot product of $Yt(\omega_l)$ and $d_l(\omega)$.

14. The system of claim 13, wherein said disturbance signals are physical vibrations, said sensors are microphones and said actuators are loudspeakers.

* * * * *